US008686031B2

United States Patent
Chiang et al.

(10) Patent No.: US 8,686,031 B2
(45) Date of Patent: Apr. 1, 2014

(54) FLAVONOIDS AND USES THEREOF (75) Inventors: Wenchang Chiang, Kaohsiung (TW); Yun-Lian Lin, Kaohsiung (TW); Cheng-Pei Chung, Kaohsiung (TW); Hong-Jhang Chen, Kaohsiung (TW)

(73) Assignee: Joben Bio-Medical Co., Ltd., Pingtung County (TW)

( * ) Notice: Subject to any disclaimer, the term of this patent is extended or adjusted under 35 U.S.C. 154(b) by 204 days.

(21) Appl. No.: 13/329,601

(22) Filed: Dec. 19, 2011

(65) Prior Publication Data
US 2013/0158107 A1  Jun. 20, 2013

(51) Int. Cl.
*A61K 31/343* (2006.01)
*C07D 307/80* (2006.01)

(52) U.S. Cl.
USPC .......................................... 514/470; 549/466

(58) Field of Classification Search
USPC .......................................... 514/470; 549/466
See application file for complete search history.

(56) References Cited

PUBLICATIONS

Salerno, L. et al., & Siracusa, Progress in the development of selective nitric oxide synthase (NOS) inhibitors, Current Pharmaceutical Design, 2002, vol. 8, No. 3, 177-200.
Peter Libby, Inflammation and cardiovascular disease mechanisms, The American Journal of Clinical Nutrition, 2006, 83(2), 456S-460S.
Raja Atreya et al., Involvement of IL-6 in the pathogenesis of inflammatory bowel disease and colon cancer, Clinical Reviews in Allergy & Immunology, 2005, vol. 28, 187-195.
James H. O'Keefe, MD. et al., Dietary strategies for improving post-prandial glucose, lipids, inflammation, and cardiovascular health, Journal of the American College of Cardiology, 2008, vol. 51, No. 3, 249-255.
Yun Lu et al., Chinese herb related molecules of cancer-cellapoptosis: A minireview of progress between Kanglaite injection and related genes, Journal of Experimental & Clinical Cancer Research, 2008, 27:31.
Ming-Yi Lee et al., Isolation and characterization of new lactam compounds that inhibit lung and colon cancer cells from adlay (*Coix lachryma-jobi* L var. ma-yuen Stapf) bran. Food and Chemical Toxicology, 2008, 46, 1933-1939.
Won-Gil Seo et al., Inhibitory effects of methanol extract of seeds of Job's tears (*Coix lachryma-jobi* L. var. ma-yuen) on nitric oxide and superoxide production in RAW 264.7 macrophages. Immunopharmacology and Immunotoxicology, 2000, 22(3), 545-554.
Hong-Jhang Chen et al., Mast cell-dependent allergic responses are inhibited by ethanolic extract of adlay (*Coix lachryma-jobi* L. var. ma-yuen Stapf) testa, Journal of Agricultural and Food Chemistry, 2010, vol. 58, No. 4, 2596-2601.
Hideaki Otsuka et al., Anti-inflammatory activity of benzoxazinoids from roots of *Coix lachryma-jobi* var. ma-yuen, Journal of Natural Products, 1988, vol. 51 No. 1, 74-79.
Ming-Yi Lee et al., Isolation and characterization of new lactam compounds that inhibit lung and colon cancer cells from adlay (*Coix lachryma-jobi* L. var. ma-yuen Stapf) bran, Food and Chemical Toxicology, 2008, 46(6), 1933-1939.
Ching-Chuan Kuo et al., 2,20-Diphenyl-1-picrylhydrazyl radical-scavenging active components from adlay (*Coix lachryma-jobi* L. var. ma-yuen Stapf) hulls, Journal of Agricultural and Food Chemistry, 2002, vol. 50, No. 21, 5850-5855.
Yen-Chou Chen et al., Inhibition of nitric oxide synthase inhibitors and lipopolysaccharide induced inducible NOS and cyclooxygenase-2 gene expressions by rutin, quercetin, and quercetin pentaacetate in RAW 264.7 macrophages, Journal of Cellular Biochemistry, 2001, 82(4), 537-548.
Uma Singh et al., Development of an in vitro screening assay to test the antiinflammatory properties of dietary supplements and pharmacologic agents, Clinical Chemistry, 2005, vol. 51 No. 12, 2252-2256.
Hong-Jhang Chen et al., Anti-inflammatory effects and chemical study of a flavonoid-enriched fraction from adlay bran, Food Chemistry, 2011, 126, 1741-1748.

*Primary Examiner* — Taofiq A Solola
(74) *Attorney, Agent, or Firm* — WPAT, P.C.; Anthony King (57) ABSTRACT

The present invention provides novel flavonoids extracted from an alcohol extract of dehulled adlay seeds. The present invention also provides a process for the preparation of the flavonoid and a method for treating inflammation in a subject, which method comprises administering to said subject an effective amount of the flavonoid and a pharmaceutically acceptable carrier or excipient.

13 Claims, 9 Drawing Sheets

FLAVONOIDS AND USES THEREOF

BACKGROUND OF THE INVENTION

1. Field of the Invention

The invention relates to novel flavonoids extracted from an alcohol extract of dehulled adlay seeds and uses thereof.

2. Description of the Related Art

Chronic inflammation contributes to the pathogenesis of a number of diseases that affect a significant part of the human population. Nitric oxide (NO) is an inorganic free radical that is implicated in pathological processes such as chronic and acute inflammation (Salerno, L., Sorrenti, V., Di Giacomo, C., Romeo, G., & Siracusa, M. A. (2002). Progress in the development of selective nitric oxide synthase (NOS) inhibitors. Current Pharmaceutical Design, 8(3), 177-200). NO is produced by the oxidation of L-arginine, catalysed by NO synthase (NOS). In the NOS family, inducible (i)NOS, in particular, is involved in the pathological overproduction of NO, and can be expressed in response to proinflammatory agents such as tumor necrosis factor (TNF)-α and lipopolysaccharide (LPS) in various cell types, including macrophages. Furthermore, activated macrophages cause inflammation, which is mediated by proinflammatory mediators, including TNF-α, interleukin (IL)-6, and NO (Libby, P. (2006). Inflammation and cardiovascular disease mechanisms. The American Journal of Clinical Nutrition, 83(2), 456S-460S). There is growing evidence that systemic inflammation is associated with increased risks of chronic diseases, such as inflammatory bowel disease and cancer (Atreya, R., & Neurath, M. F. (2005). Involvement of IL-6 in the pathogenesis of inflammatory bowel disease and colon cancer. Clinical Reviews in Allergy & Immunology, 28(3), 187-196). Therefore, the application of dietary components, aside from anti-inflammatory drugs, has become a focus of interest. Diets for preventing chronic diseases associated with inflammation were recently proposed as a therapeutic strategy (O'Keefe, J. H., Gheewala, N. M., & O'Keefe, J. O. (2008). Dietary strategies for improving post-prandial glucose, lipids, inflammation, and cardiovascular health. Journal of the American College of Cardiology, 51(3), 249-255).

Adlay (Job's tears, *Coix lachryma-jobi* L. var. *ma-yuen* Stapf) is an annual crop, which has long been used in Chinese medicine to treat warts, chapped skin, rheumatism, and neuralgia (Lu, Y., Li, C. S., & Dong, Q. (2008). Chinese herb related molecules of cancer-cell apoptosis: A minireview of progress between Kanglaite injection and related genes. Journal of Experimental & Clinical Cancer Research, 27, 31). It was reported to have various activities, such as anticancer (Lee, M. Y., Lin, H. Y., Cheng, F., Chiang, W., & Kuo, Y. H. (2008). Isolation and characterization of new lactam compounds that inhibit lung and colon cancer cells from adlay (*Coix lachryma-jobi* L. var. *ma-yuen* Stapf) bran. Food and Chemical Toxicology, 46(6), 1933-1939), anti-inflammatory (Seo, W. G., Pae, H. O., Chai, K. Y., Yun, Y. G., Kwon, T. H., & Chung, H. T. (2000). Inhibitory effects of methanol extract of seeds of Job's tears (*Coix lachryma-jobi* L. var. *ma-yuen*) on nitric oxide and superoxide production in RAW 264.7 macrophages. Immunopharmacology and Immunotoxicology, 22(3), 545-554), and antiallergic effects (Chen, H. J., Shih, C. K., Hsu, H. Y., & Chiang, W. (2010). Mast cell-dependent allergic responses are inhibited by ethanolic extract of adlay (*Coix lachryma-jobi* L. var. *ma-yuen* Stapf) testa. Journal of Agricultural and Food Chemistry, 58(4), 2596-2601). Various constituents were isolated from adlay, such as anti-inflammatory benzoxazinoids from the roots (Otsuka, H., Hirai, Y., Nagao, T., & Yamasaki, K. (1988). Anti-inflammatory activity of benzoxazinoids from roots of *Coix lachryma-jobi* var. *ma-yuen*. Journal of Natural Products, 51(1), 74-79), phenolic compounds with antiallergic properties from the testa (Chen, H. J., Shih, C. K., Hsu, H. Y., & Chiang, W. (2010). Mast cell-dependent allergic responses are inhibited by ethanolic extract of adlay (*Coix lachryma-jobi* L. var. *ma-yuen* Stapf) testa. Journal of Agricultural and Food Chemistry, 58(4), 2596-2601), cytotoxic lactams from the bran (Lee, M. Y., Lin, H. Y., Cheng, F., Chiang, W., & Kuo, Y. H. (2008). Isolation and characterization of new lactam compounds that inhibit lung and colon cancer cells from adlay (*Coix lachryma-jobi* L. var. *ma-yuen* Stapf) bran. Food and Chemical Toxicology, 46(6), 1933-1939), and antioxidative lignans from the hulls (Kuo, C. C., Chiang, W., Liu, G. P., Chien, Y. L., Chang, J. Y., Lee, C. K., et al. (2002). 2,20-Diphenyl-1-picrylhydrazyl radical-scavenging active components from adlay (*Coix lachryma-jobi* L. var. *ma-yuen* Stapf) hulls. Journal of Agricultural and Food Chemistry, 50(21), 5850-5855). However, anti-inflammatory and related components of adlay bran, the edible part of adlay, are still unclear.

SUMMARY OF THE INVENTION

In the present invention, novel flavonoids extracted from an alcohol extract of dehulled adlay seeds are provided. Moreover, anti-inflammatory effect of the flavonoids with in vitro and ex vivo cell cultures is proven.

The invention provides a flavonoid of formula (I):

formula (I)

or a pharmaceutically acceptable derivative thereof, wherein $R_1$ is H or an alkyl group having 1 to 6 carbon atoms.

The invention also provides a composition comprising the flavonoid as mentioned above and optionally a pharmaceutically acceptable carrier or excipient.

The invention further provides a process for the preparation of the flavonoid as mentioned above, which process comprises the steps of:

(a) providing adlay bran from dehulled adlay seeds;
(b) extracting the adlay bran in step (a) with an alcohol solution to obtain an alcohol extract;
(c) sequential partitioning the ethanol extract in step (b) with hexane and ethyl acetate to obtain an ethyl acetate fraction;
(d) subfractioning the ethyl acetate fraction in step (c) with column chromatography with successive elution by an ethyl acetate/hexane gradient ant methanol solvent to obtain an about 40% to about 60% ethyl acetate/hexane subfration; and
(e) isolating the flavonoid from the subfraction in step (d) by high-performance liquid chromatography.

The invention also provides a method for treating inflammation in a subject, which comprises administering to said subject an effective amount of the flavonoid as mentioned above and a pharmaceutically acceptable carrier or excipient.

DETAILED DESCRIPTION OF THE INVENTION

The present invention can be more readily understood by reference to the following detailed description of various embodiments of the invention, the examples, and the chemical drawings and tables with their relevant descriptions. It is to be understood that unless otherwise specifically indicated by the claims, the invention is not limited to specific preparation methods, carriers or formulations, or to particular modes of formulating the compounds of the invention into products or compositions intended for topical, oral or parenteral administration, because as one of ordinary skill in the relevant arts is well aware, such things can, of course, vary. It is also to be understood that the terminology used herein is for the purpose of describing particular embodiments only and is not intended to be limiting.

As utilized in accordance with the present disclosure, the following terms, unless otherwise indicated, shall be understood to have the following meaning:

As used herein, the term "alkyl" includes straight and branched chains.

"Alkyl" refers to a hydrocarbon group that can be conceptually formed from an alkane by removing hydrogen from the structure of a non-cyclic hydrocarbon compound having straight or branched carbon chains, and replacing the hydrogen atom with another atom or organic or inorganic substituent group. In some embodiments of the invention, the "alkyl group having 1 to 6 carbon atoms" such as methyl, ethyl, propyl, isopropyl, n-butyl, iso-butyl, sec-butyl, tert-butyl, amyl, tert-amyl, hexyl and the like.

The term "a pharmaceutically acceptable derivative" or "pharmaceutically acceptable derivatives" as used herein denotes a compound that is modified from the compound of the invention but that has properties and efficacies that are the same as or better than those of the compound of the invention. Preferably, the pharmaceutically acceptable derivative is a pharmaceutically acceptable salt, solvate, hydrate, or prodrug of the compound of the invention.

One or more of the compounds of the invention may be present as a salt. The term "salt" encompasses those salts formed with the organic and inorganic anions and cations. Furthermore, the term includes salts that form by standard acid-base reactions with basic groups and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, and cinnamic acids.

The compounds of the invention can also exist as solvates and hydrates. Thus, these compounds may crystallize with, for example, waters of hydration, or one, a number of, or any fraction of molecules of the mother liquor solvent. The solvates and hydrates of such compounds are included within the scope of this invention.

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint. As used herein the term "about" refers to ±10%.

"Optional" or "optionally" means that the subsequently described event or circumstance may or may not occur, and that the description includes instances where said event or circumstance occurs and instances where it does not. For example, the phrase "optionally comprising an agent" means that the agent may or may not exist.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The term "subject" as used herein denotes any animal, preferably a mammal, and more preferably a human. The examples of subjects include humans, non-human primates, rodents, guinea pigs, rabbits, sheep, pigs, goats, cows, horses, dogs and cats.

The term "effective amount" of an active ingredient as provided herein means a sufficient amount of the ingredient to provide the desired regulation of a desired function, such as gene expression, protein function, or the induction of a particular type of response. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "treating" or "treatment" as used herein denotes reversing, alleviating, inhibiting the progress of, or improving the disorder or condition to which such term applies, or one or more symptoms of such disorder or condition.

The term "carrier" or "excipient" as used herein refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a capsule or tablet suitable for oral administration. Suitable carriers or excipients are well known to persons of ordinary skill in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, mannitol, sorbitol, glycerol or powder, polymers (such as polyvinyl-pyrrolidone, polyvinyl alcohol, and polyethylene glycols), and other pharmaceutically acceptable materials. The carrier should not destroy the pharmacological activity of the therapeutic agent and should be non-toxic when administered in doses sufficient to deliver a therapeutic amount of the agent.

The invention provides a flavonoid of formula (I):

formula (I)

or a pharmaceutically acceptable derivative thereof, wherein $R_1$ is H or an alkyl group having 1 to 6 carbon atoms.

In some preferred embodiments of the flavonoid of formula (I), $R_1$ is a methyl group.

In a more preferred embodiment of the invention, the flavonoid of formula (I) is 2',6-dihydroxy-4'-methoxydihydroauronol.

The flavonoid of the invention is preferably further converted into a pharmaceutically acceptable derivative, such as a pharmaceutically acceptable salt, solvate or prodrug, by any known methods.

The present invention also provides a composition comprising the flavonoid of formula (I) or a pharmaceutically acceptable derivative thereof. The composition of the invention is preferably a food composition or a pharmaceutical composition. The flavonoid of formula (I) of the present invention is preferably provided in the form of an alcohol extract of dehulled adlay seeds or a chemical compound.

The flavonoid of formula (I) or a pharmaceutically acceptable derivative thereof or the alcohol extract of dehulled adlay seeds containing the flavonoid of formula (I) or a pharmaceutically acceptable derivative thereof can be added to a conventional food composition (i.e. the edible food or drink or precursors thereof) in the manufacturing process of the food composition. Almost all food compositions can be supplemented with the alcohol extract of dehulled adlay seeds of the invention. The food compositions that can be supplemented with the alcohol extract of dehulled adlay seeds of the invention include, but are not limited to, candies, baked goods, ice creams, dairy products, sweet and flavor snacks, snack bars, meal replacement products, fast foods, soups, pastas, noodles, canned foods, frozen foods, dried foods, refrigerated foods, oils and fats, baby foods, or soft foods painted on breads, or mixtures thereof.

The pharmaceutical composition of the invention is preferably administered topically or systemically by any method known in the art, including, but not limited to, intramuscular, intradermal, intravenous, subcutaneous, intraperitoneal, intranasal, oral, mucosal or external routes. The appropriate route, formulation and administration schedule can be determined by those skilled in the art. In the present invention, the pharmaceutical composition can be formulated in various ways, according to the corresponding route of administration, such as a liquid solution, a suspension, an emulsion, a syrup, a tablet, a pill, a capsule, a sustained release formulation, a powder, a granule, an ampoule, an injection, an infusion, a kit, an ointment, a lotion, a liniment, a cream or a combination thereof. If necessary, it may be sterilized or mixed with any pharmaceutically acceptable carrier or excipient, many of which are known to one of ordinary skill in the art; see paragraph [0028] for example.

Figure 1:
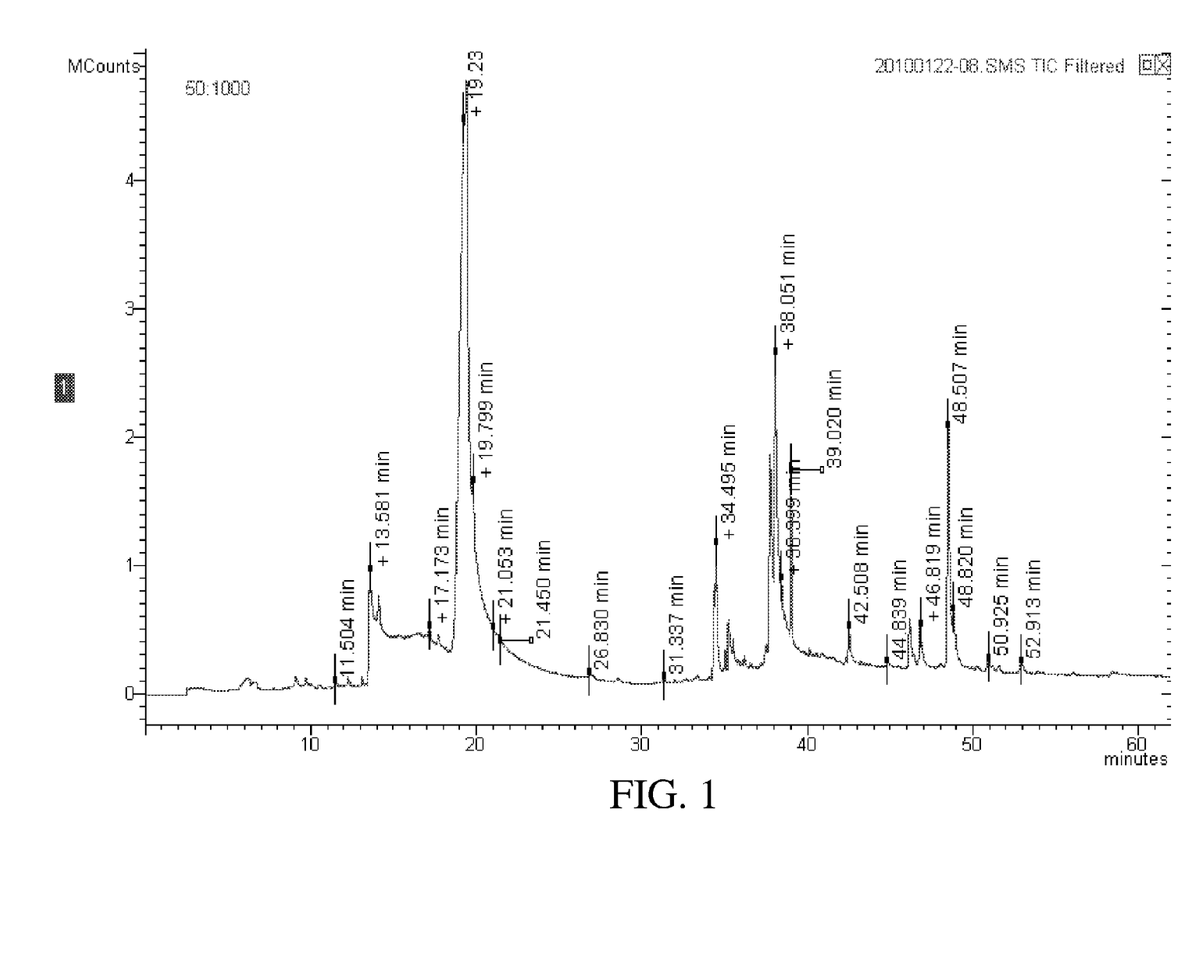
FIG. 1 illustrates the GC-MS spectrogram of the alcohol extract of dehulled adlay seeds according to the invention.

In one preferred embodiment of the invention, the alcohol extract of dehulled adlay seeds is subjected to a Gas Chromatography-Mass Spectrophotometry (GC-MS) assay. The gas chromatography is conducted with Varian® 450-GC; and the mass spectrophotometry is conducted with Varian® 240-MS; the column is Varian® VF-5 ms 30 m×0.25 mm (I.D. 0.25 μm). The temperature program is 150° C. for 5 min; heating to 200° C. at a rate of 10° C./min for 20 min; and heating to 280° C. at a rate of 10° C./min for 25 min. As shown in FIG. 1, the spectrogram obtained comprises peaks at retention time of about 13.581 min, about 19.237 min, 19.334 min, about 19.435 min, about 19.799 min, about 37.75 min, about 38.051 min, about 48.504 min and about 48.819 min (Table 1).

TABLE 1

| Retention time (min) | Area (%) |
|---|---|
| 13.581 | 2.65 |
| 19.237 | 35.17 |
| 19.334 | 6.68 |
| 19.435 | 20.60 |
| 19.799 | 4.11 |
| 37.75 | 7.70 |
| 38.051 | 11.94 |
| 48.504 | 8.56 |
| 48.819 | 2.60 |

Figure 2:
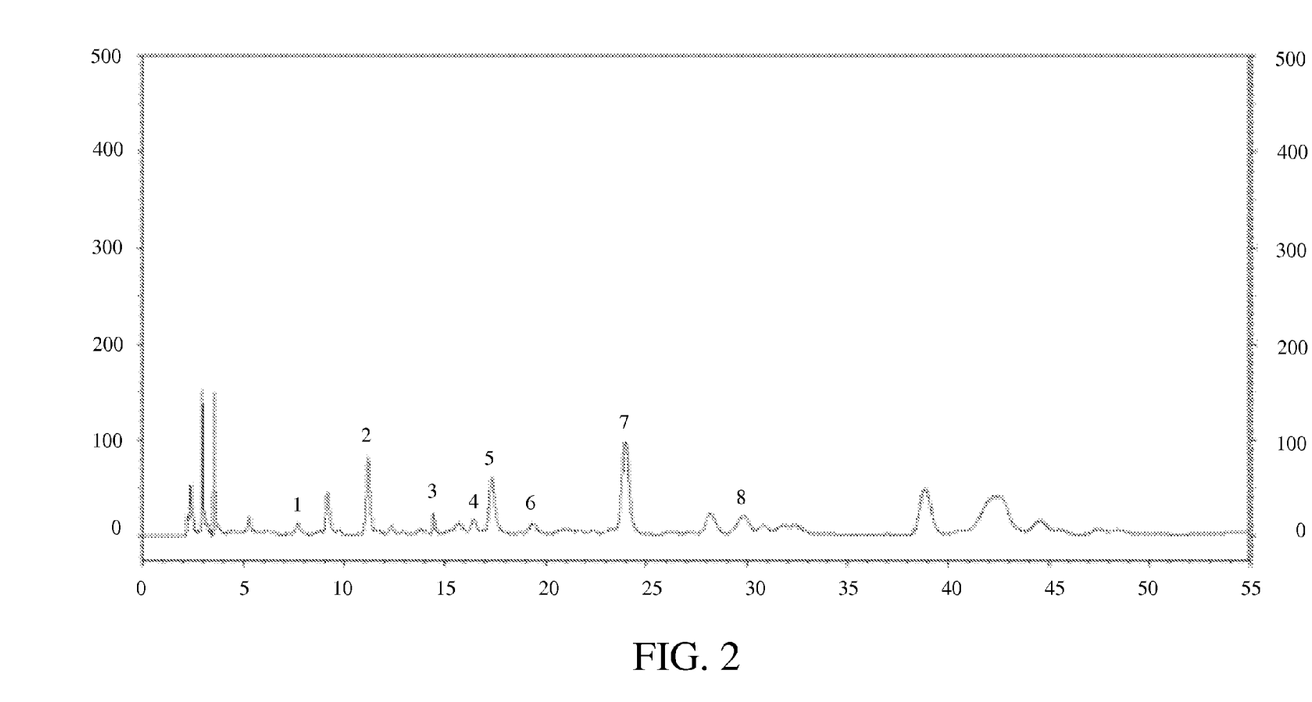
FIG. 2 illustrates the HPLC spectrogram of the alcohol extract of dehulled adlay seeds according to the invention.

In one preferred embodiment of the invention, the alcohol extract of dehulled adlay seeds is subjected to a high performance liquid chromatography assay. The column is Reverse phase C18 column (250×4.6 mm i.d.; YMC Co., INC). The column temperature is 40° C. The chromatograms are extracted at 280 nm and 320 nm. The mobile phase uses Solution A: 5% acetic acid in water; Solution B: 0.5% acetic acid in water/100% acetonitrile (1:1, v/v). The gradient elution program is shown in Table 2. As shown in FIG. 2, the spectrogram obtained comprises peaks at retention time of about 7.5 min, about 12.1 min, 14.4 min, about 16.1 min, about 16.8 min, about 18.9 min, about 23.3 min, and about 29.1 min.

TABLE 2

| Time (min) | Flow rate (mL/min) | Mobile phase A (%) | Mobile phase B (%) |
|---|---|---|---|
| 0 | 1.0 | 90 | 10 |
| 10 | 1.0 | 85 | 15 |
| 20 | 1.0 | 84 | 16 |
| 35 | 1.0 | 83 | 17 |
| 50 | 1.0 | 79 | 21 |
| 55 | 1.0 | 79 | 21 |

The dehulled adlay seed comprises bran and endosperm, therefore, the alcohol extract of dehulled adlay seeds according to the invention preferably comprises an alcohol extract of adlay bran. The manner for obtaining the bran from the dehulled adlay seeds is well-known to artisans skilled in this field.

In one preferred embodiment of the invention, the alcohol extract of dehulled adlay seeds is an ethanol extract of dehulled adlay seeds.

In one preferred embodiment of the invention, the flavonoid of formula (I) of the present invention is preferably provided in the form of an ethyl acetate sub-fraction of the alcohol extract of dehulled adlay seeds.

In one preferred embodiment of the invention, the flavonoid is prepared according to a process comprising the steps of:
(a) providing adlay bran from dehulled adlay seeds;
(b) extracting the adlay bran in step (a) with an ethanol solution to obtain an ethanol extract;
(c) sequential partitioning the ethanol extract in step (b) with hexane and ethyl acetate to obtain an ethyl acetate fraction;
(d) subfractioning the ethyl acetate fraction in step (c) with column chromatography with successive elution by an ethyl acetate/hexane gradient and methanol solvent to obtain an about 40% to about 60% ethyl acetate/hexane subfraction; and
(e) isolating the flavonoid from the subfraction in step (d) by high-performance liquid chromatography.

The term "dehulled adlay seeds" as used herein refers to seeds of adlay without hulls, testas, coverings, shells, or pods. The manner of removing the hulls, coverings, shells or pods from the adlay seeds is well-known to artisans skilled in this field. If needed, the bran and/or endosperm is further isolated from the dehulled adlay seeds.

The adlay seeds referred to in this invention are not particularly limited. Preferably, the adlay belongs to Gramineae family, Panicoideae sub-family, and *Coix* species, or Poales order, Poaceae family, and *Coix* species. More preferably, the adlay is *Coix lachryma-jobi, Coix lachryma-jobi* L., *Coix lachryma-jobi* L. var. *ma-yuen* Stapf, *Coix agrestis Lour., Coix arundinacea Lam., Coix exaltata Jacq., Coix lacryma* L.

According to the process of the invention, prior to the step (a), the dehulled adlay seeds are preferably dried.

In one preferred embodiment of the invention, prior to the step (b), the adlay bran is cut into pieces, and more preferred, the pieces of the adlay brain is further blended into powder. The manner of cutting and/or blending is well-known to artisans skilled in this field.

The term "an alcohol extract of dehulled adlay seeds" as used herein refers to an extract of dehulled adlay seeds obtained by extracting the seeds with an alcohol solution. The manner of extracting the seeds with a solution is well-known to artisans skilled in this field. In one preferred embodiment of the invention, the dehulled adlay seeds are soaked in an alcohol solution for extraction.

The ratio (w/v) of the dehulled adlay seeds and the alcohol solution is not specifically restricted, and can be about 1:1 to about 1:10; preferably about 1:3 to about 1:8; and most preferably about 1:5.

In one preferred embodiment of the invention, the alcohol is selected from the group consisting of methanol, ethanol, n-propanol, isopropanol, n-butanol, iso-butanol, sec-butanol, tert-butanol, and ethanol acetate. More preferably, the alcohol is methanol or ethanol; most preferably, the alcohol is ethanol. The alcohol solution preferably about 90% to about 99.9% ethanol.

Preferably, the step (b) further comprises obtaining a liquid fraction from the extract, and a solid fraction is removed. The manner of removing the solid fraction to obtain the liquid fraction is well-known to artisans skilled in this field.

The invention also provides a method for treating inflammation in a subject, which comprises administering to said subject an effective amount of the flavonoid as mentioned above and a pharmaceutically acceptable carrier or excipient.

The following examples are given for the purpose of illustration only and are not intended to limit the scope of the present invention.

EXAMPLE

Materials and Methods

Preparation of the Ethanol Extract and Various Fractions from the Bran of Adlay Seeds and Isolation and Identification of the Flavonoid Adlay seeds are collected and divided into the hull, testa, and dehulled adlay by gentle blowing with an electric fan. The dehulled adlay, the edible part of adlay seed, is separated into the bran and polished adlay. Adlay bran powder (2 kg) is extracted three times with 20 L of ethanol at room temperature for 2 weeks. The ethanol extracts are combined and concentrated under reduced pressure in a rotary vacuum evaporator. The dry ethanol extract (ABE, 365 g) is suspended in 4 L of 90% MeOH in $H_2O$, followed by sequential partitioning with hexane, ethyl acetate (EtOAc), and n-butanol (BuOH), to give hexane-soluble (ABE-Hex, 155 g), ethyl-acetate-soluble (ABE-EtOAc, 145 g), n-butanol-soluble (ABE-BuOH, 12 g), and water-soluble fractions (ABE-$H_2O$, 47 g). ABE-EtOAc was then subjected to silica gel (230-400 mesh) column chromatography with successive elution by a Hex/EtOAc gradient and MeOH solvent system. Subfractions with the same thin-layer chromatography (TLC) patterns were combined into one fraction; thus 9 fractions were obtained: A (~0% to ~20% EtOAc/Hex), B (~20% to ~25% EtOAc/Hex), C (~25% to ~30% EtOAc/Hex), D (~30% to ~40% EtOAc/Hex), E (~40% to ~60% EtOAc/Hex), F (~60% to ~80% EtOAc/Hex), G (~80% to ~90% EtOAc/Hex), H (~90% to ~100% EtOAc/Hex), and I (100% MeOH). The activities of various subfractions are tested in the system described below, and the bioactive subfractions, ABE-EtOAc-E-I are combined (28.3 g) and further purified over a Sephadex LH-20 column (eluted with MeOH) and semi-preparative high-performance liquid chromatography (HPLC) on a LiChrosorb Si-60 column, using a mobile phase of acetone: EtOAc: Hex of 2:1:5 at a flow rate of 1.5 ml/min to yield the 2',6-dihydroxy-4'-methoxydihydroauronol (1.2 mg).

2',6-Dihydroxy-4'-methoxydihydroauronol (1). Amorphous powder. ESIMS: m/z 289 [M+H]$^+$; $[\alpha]^{25}_D$=+13.3° (c 0.3, $CH_3OH$); CD (c 0.035, MeOH) 287.7 (+0.58), 238.9 (−1.32), 212.2 (−1.75), 207.1 (−2.40); IR $\nu_{max}$ 3334, 1623, 1461, 1374, 1255, 1148 cm$^{-1}$; UV (MeOH)(log ϵ)$\lambda_{max}$ 282 (3.78), 286 (3.79) nm; $^1$H NMR ($CD_3OD$, 500 MHz): δ 3.51 (1H, dd, J=14.5, 7.5, H-9α), 3.53 (1H, dd, J=14.5, 6.0, H-9β), 3.73 (3H, s, 4'-$OCH_3$), 4.21 (1H, br d, J=6.6, H-7), 5.46 (1H, m, H-8), 6.29 (1H, d, J=2.4, H-1), 6.37 (1H, d, J=2.4, H-3'), 6.43 (1H, dd, J=8.4, 2.4, H-5'), 6.48 (1H, dd, J=8.4, 2.4, H-5), 7.16 (1H, d, J=8.4, H-6'), 7.28 (1H, d, J=8.4, H-4); $^{13}$C NMR ($CD_3OD$, 125 MHz): δ 40.9 (t, C-9), 55.9 (q, $OCH_3$), 67.5 (d, C-7), 80.1 (d, C-8), 97.5 (d, C-1), 104.0 (d, C-3'), 107.3 (d, C-6'), 110.7 (d, C-5), 112.9 (s, C-3), 120.9 (s, C-1'), 126.0 (d, C-5'), 133.2 (d, C-4), 158.0 (s, C-2), 160.8 (s, C-6), 162.0 (s, C-2'), 162.5 (s, C-4'); key H-H COSY correlations: H-9/H-8/H-7; key HMBC correlations: H-7/C-2 & C-8, H-4/C-2 & C-6, H-8/C-2 & C-7, H-3'/C-2' & C-4', H-3'/C-2' & C-4', H-5' & 4'-$OCH_3$/C-4', H-5/C-3, H-6'/C-2' & C-4'; key NOESY correlations: H-9/H-7, H-8 & H-6', 4'-$OCH_3$/H-3' & H-5', H-4/H-5.

Cell Culture

Mouse macrophage cells of the RAW264.7 cell line are obtained from the Bioresource Collection and Research Centre (BCRC, Food Industry Research and Development Institute, Hsinchu, Taiwan) and are cultured in DMEM containing 10% heat-inactivated FBS, 100 U/ml of penicillin-streptomycin, and 2% glutamine in a 5% $CO_2$ incubator at 37° C. Cells are detached by washing and scraping. After washing, cells are resuspended in fresh medium and used for subsequent experiments.

Preparation of Peritoneal Macrophages

BALB/c mice (6-7 weeks old, 19-25 g) are purchased from LASCO (BioLASCO, Taipei, Taiwan). Mice are kept in an air conditioned, pathogen-free room at a temperature of 23±2° C. on a regulated 12-h light/dark cycle. They are housed individually in stainless-steel wire cages and fed a commercial diet (Lab Rodent Chow 5001, Ralston Purina, St. Louis, Mo., USA). Animal care and handling are conformed to accepted guidelines, and are approved by the Institutional Animal Care and Use Committee of National Taiwan University. Murine peritoneal macrophages are collected from the peritoneal cavity of normal BALB/c mice. Briefly, peritoneal fluid is collected by an intraperitoneal (i.p.) injection of 10 ml of ice-cold DMEM. After washing with RBC lysis buffer, peritoneal macrophages are centrifuged and grown in DMEM supplemented with 10% FBS and the antibiotic-antimycotic. Cells are seeded at $10^6$ cells/well and allowed to adhere for 2 h at 37° C. in 5% $CO_2$. After non-adherent cells are removed by washing with PBS, adherent cells were used for subsequent experiments.

Assay of Cell Viability

Cell viabilities of RAW264.7 cells and murine peritoneal macrophages are determined by an MTT assay, as previously reported (Chen, H. J., Shih, C. K., Hsu, H. Y., & Chiang, W. (2010). Mast cell-dependent allergic responses are inhibited by ethanolic extract of adlay (*Coix lachryma-jobi* L. var. *ma-yuen* Stapf) testa. Journal of Agricultural and Food Chemistry, 58(4), 2596-2601). The cell viability of various test groups is determined by the equation: (absorbance of the test group/absorbance of the control)×100%. All test samples mentioned above are dissolved in DMSO, and the final concentration of DMSO is <0.1%; 0.1% DMSO is used as the control group.

Assay of NO Release

An NO release assay is carried out according to the method described by Matsuda, Morikawa, Ando, Toguchida, and Yoshikawa (Matsuda, H., Morikawa, T., Ando, S., Toguchida, I., & Yoshikawa, M. (2003). Structural requirements of flavonoids for nitric oxide production inhibitory activity and mechanism of action. Bioorganic & Medicinal Chemistry, 11(9), 1995-2000). Briefly, RAW264.7 cells are seeded at $10^5$ cells/well in a 96-well plate. After washing with PBS, cells are pretreated with various test samples and 1 µg/ml of LPS for 24 h. The supernatant (100 µL) is mixed with the same volume of Griess reagent (1% sulphanilamide in 5% phosphoric acid and 0.1% N-(1-naphthyl)ethylenediamine dihydrochloride in water) and incubated for 15 min in the dark. The absorbance of the water-soluble purplish-red product is read at 570 nm with an enzyme-linked immunosorbent assay (ELISA) reader. The amount of NO is calculated by a calibration curve established with 0.15-100 µM $NaNO_2$.

Measurement of IL-6 and TNF-α

The inhibitory effects on LPS-stimulated release of cytokines in RAW264.7 cells and murine peritoneal macrophages are evaluated, as described above. Briefly, RAW264.7 cells and murine peritoneal macrophages are treated with various test samples and stimulated with 1 or 10 µg/ml of LPS for 24 and 48 h. The concentrations of IL-6 and TNF-α in the supernatants are determined by commercially available ELISA kits (eBioscience, San Diego, Calif., USA).

HPLC/MS Analysis

HPLC analyses are carried out using a Finnigan MAT HPLC system (Thermo Electron, Akron, Ohio, USA), which is equipped with an analytical Inertsil® ODS-3 column (4.6× 250 mm×5 µm) and a guard column at a constant flow rate of 0.3 ml/min. The mobile phases A (0.01% formic acid in double-distilled water, pH 3.30) and B (acetonitrile: methanol 1:1, v/v) are used according to a programmed protocol: 0-10 min, 30-40% B; 10-20 min, 40-60% B; 20-27 min, 60-75% B; 27-35 min, 75-78% B; 35-40 min, 78-85% B; 40-50 min, 85-95% B; and 50-70 min, 95% B. The UV detector is operated at a wavelength of 254 nm. This system was coupled with a Finnigan MAT LCQ ion trap mass spectrometer system (Finnigan MAT, San Jose, Calif., USA) which is operated in the electrospray ionisation (ESI) mode. An aliquot of the bioactive fraction (20 µl) is directly introduced into the column through the autosampler (Finnigan MAT AS3000), where nitrogen is used as the nebulising and drying gas. The operating parameters used are as follows: a gas temperature of 250° C., a spray needle voltage of 5 kV, a nebulizer pressure of 60 psi, and auxiliary gas of 30 psi. An ion trap, containing helium damping gas, is introduced, following the manufacturer's protocols. The mass spectra are acquired in an m/z range of 100-1000 with 5 microscans and a maximum ion injection time of 200 ms.

Statistical Analysis

Results are expressed as the means±standard deviation (SD) of three experiments. Differences between specific means are analyzed by one-way analysis of variance (ANOVA), using the SPSS system vers. 11.0 (SPSS, Chicago, Ill., USA). Group means are compared using one-way ANOVA, followed by Dunnett's test. Probability values (p) of <0.05 are considered statistically significant.

Results and Discussion

Effects of Subfractions on NO Release and Cell Viability

Figure 3:
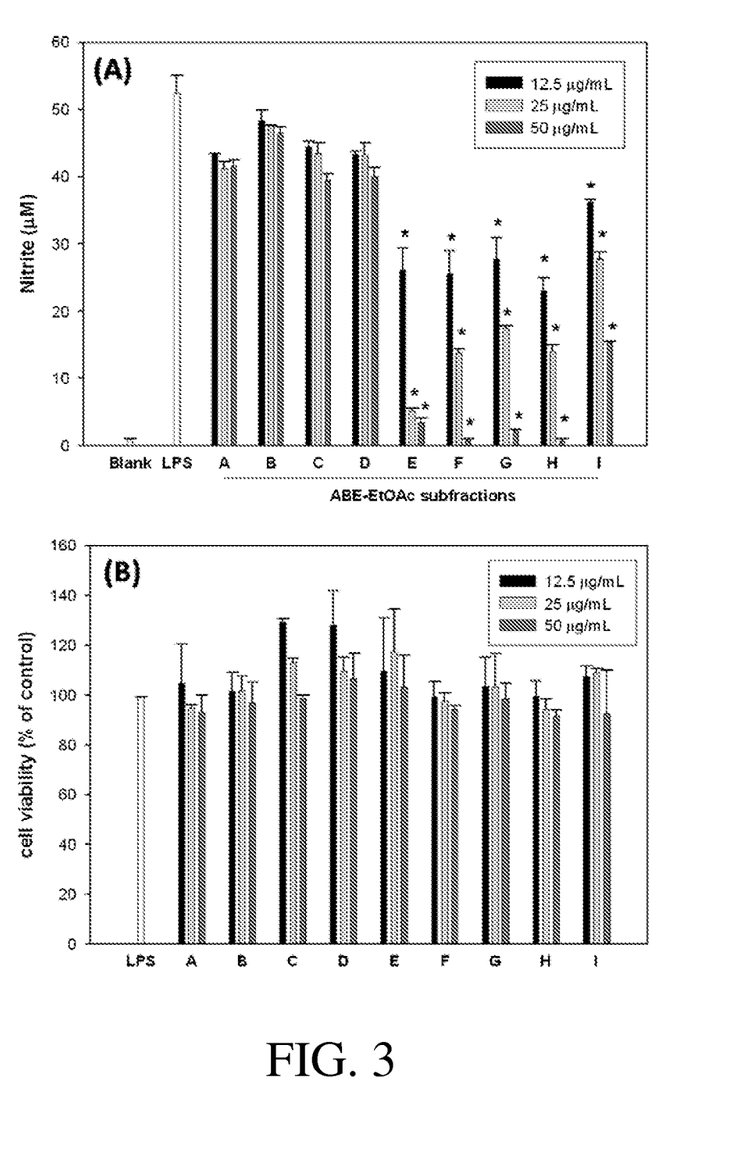
FIG. 3 illustrates the effects of ABE-EtOAc subfractions of the ethanol extract on (A) nitrite production and (B) cell viability in LPS-stimulated RAW264.7 cells. Each column represents the mean±SD of three experiments. RAW264.7 cells were stimulated by 1 µg/ml of lipopolysaccharide (LPS) for 24 h.

NO formation and cytokine secretions suggested a high correlation with various pathophysiological processes, including inflammation (Chen, Y. C., Shen, S. C., Lee, W. R., Hou, W. C., Yang, L. L., & Lee, T. J. (2001). Inhibition of nitric oxide synthase inhibitors and lipopolysaccharide induced inducible NOS and cyclooxygenase-2 gene expressions by rutin, quercetin, and quercetin pentaacetate in RAW 264.7 macrophages. Journal of Cellular Biochemistry, 82(4), 537-548). The suppressive effect of the ABE-EtOAc on the production of NO is evaluated in LPS-stimulated RAW264.7 cells. As shown in FIG. 3A, LPS significantly increases NO production compared to the unstimulated control, and subfractions ABE-EtOAc-E-I (40-100% EtOAc/Hex) presents significant inhibition of NO production at the concentration of 25 µg/mL, but the other subfractions do not. These data indicate that major anti-inflammatory components possibly exist in the 40-100% EtOAc/Hex subfractions of the ABE-EtOAc. For the cytotoxicity assay, cell viability showed no significant difference between the control and ABE-EtOAc-E-I subfractions (12.5-50 µg/ml) (FIG. 3B). Therefore, these five subfractions were subjected to further investigation.

Effects of Subfractions of the ABE-EtOAc on the Secretion of Cytokines

Figure 4:
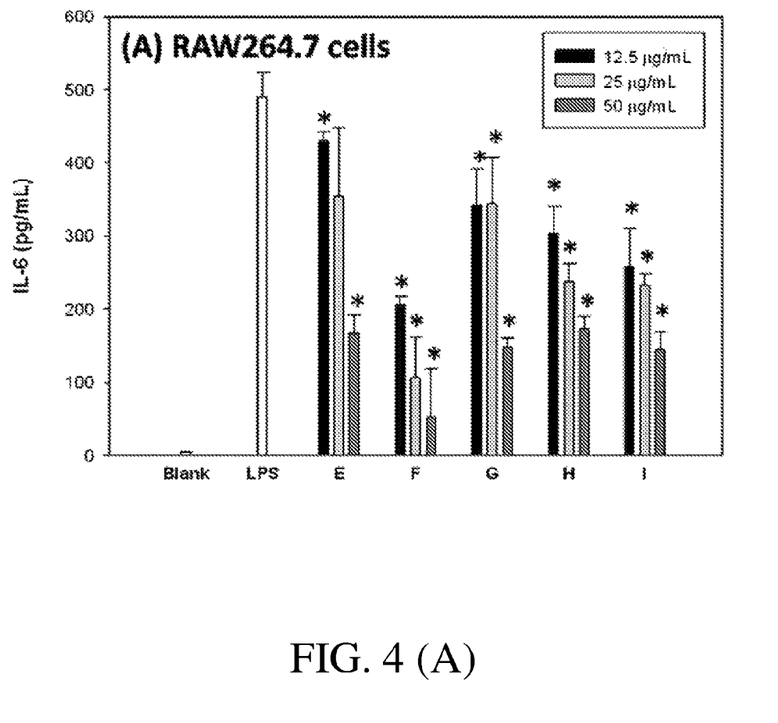
FIG. 4 illustrates the effects of ABE-EtOAc subfractions on proinflammatory cytokine production from LPS-stimulated RAW264.7 cells and peritoneal macrophages. Values are expressed as the means±SD of three independent experiments, each with triplicates and statistically analyzed using Student's t-test. *$p<0.05$, indicates a significant difference from the control. RAW264.7 cells are stimulated by 1 µg/mL of LPS for 24 h of incubation. Murine peritoneal macrophages are stimulated by 10 µg/mL of LPS for 48 h of incubation.

IL-6 and TNF-α are well-known inflammatory mediators that modulate acute and chronic inflammatory conditions (Libby, P. (2006). Inflammation and cardiovascular disease mechanisms. The American Journal of Clinical Nutrition, 83(2), 456S-460S). Macrophage cell lines, such as murine RAW264.7 and human THP-1 cells, have been used as rapid in vitro screening methods to study anti-inflammatory agents (Singh, U., Tabibian, J., Venugopal, S. K., Devaraj, S., & Jialal, I. (2005). Development of an in vitro screening assay to test the antiinflammatory properties of dietary supplements and pharmacologic agents. Clinical Chemistry, 51(12), 2252-2256). In the Example, RAW264.7 cells and murine peritoneal macrophages are used for screening. As shown in FIG. 4, ABE-EtOAc subfractions (50 µg/ml) significantly inhibit IL-6 and TNF-α production in both LPS-stimulated RAW264.7 cells and peritoneal macrophages. Inhibition of IL-6 secretion occurred in the order ABE-EtOAc-F (89%) >ABE-EtOAc-I (70%)>ABE-EtOAc-G (69%)>ABE-EtOAc-E (65%)>ABE-EtOAc-H (64%) at the concentration of 25 µg/ml in LPS-stimulated RAW264.7 cells (FIG. 4A). Similar results are obtained for IL-6 secretion in a concentration-dependent manner in LPS-stimulated peritoneal macrophages (FIG. 4C). Although only modest inhibition of TNF-a secretion is observed at the concentrations of 12.5 and 25 µg/ml, high concentrations (50 µg/ml) of each ABE-EtOAc subfraction effectively diminish TNF-α production in LPS-stimulated RAW264.7 cells by up to 48% (FIG. 4B). The generation of TNF-α is also concentration-dependently decreased in LPS-stimulated murine peritoneal macrophages (FIG. 4D). Meanwhile, pretreatment of RAW264.7 cells and primary peritoneal macrophages with 12.5, 25, and 50 µg/mL subfractions of the ABE-EtOAc for 24 h had no direct cytotoxicity according to an MTT assay (data not shown).

Identification of Isolated Compounds from the ABE-EtOAc and their Effects on NO Production The ABE is successively partitioned with Hex, EtOAc, and n-BuOH to yield Hex-, EtOAc-, n-BuOH-, and $H_2O$-soluble fractions. The EtOAc fraction shows an anti-inflammatory effect, when subjected to column chromatography over silica gel. Bioactive subfractions E-I are combined and then subjected to further chromatography, using Sephadex LH-20 and semi-preparative silica gel columns.

2',6-dihydroxy-4'-methoxydihydroauronol (compound 1) is obtained as a colorless amorphous powder. The ESIMS spectrum of 2',6-dihydroxy-4'-methoxydihydroauronol showed a quasi-molecular ion peak at m/z 289 [M+H]$^+$. The UV spectrum displayed absorption peaks at 282 and 286 nm. The IR spectrum suggests the presence of hydroxyl (3334 and 1148 cm$^{-1}$) and aromatic moieties (1623 cm$^{-1}$). $^1$H and $^{13}$C NMR spectra show three ABX-type signals at $\delta_H$ 3.51 (dd, J=14.5, 7.5), 3.53 (dd, J=14.5, 6.0), and 5.46 (m), $\delta_C$ 40.9 (t) and 80.1 (d); $\delta_H$ 6.29 (d, J=2.4), 6.48 (d, J=8.4, 2.4) and 7.28 (d, J=8.4), $\delta_C$ 97.5 (d), 110.7 (d) and 133.2 (d); $\delta_H$ 6.37 (d, J=2.4), 6.43 (dd, J=8.4, 2.4), and 7.16 (d, J=8.4), $\delta_C$ 126.0 (d), 104.0 (d), and 107.3 (d), a methoxy group ($\delta_H$ 3.73; $\delta_C$ (55.9 (q)), and an oxymethine proton [$\delta_H$ 4.21 (br d, J=6.6); $\delta_C$ (67.5 (d)]. The H-H COSY spectrum shows a spin-spin coupling partner sequence H-9/H-8/H-7. The connectivities of the A-ring and C-ring, and C-ring and Bring are determined by key HMBC correlations at H-7/C-2 and C-8, H-4 and H-8/C-2, H-3'/C-2' and C-4', H-3'/C-2' and C-4', H-5 and 4'-OCH$_3$/C-4', H-5/C-3. Further structural confirmation is obtained from the NOESY spectrum, where correlations are seen of H-9 with H-7, H-8 and H-6', and of methoxyl with H-3' and H-5'. From the above results, the structure of the compound is assigned as 2',6-dihydroxy-4'-methoxydihydroauronol.

Figure 5:
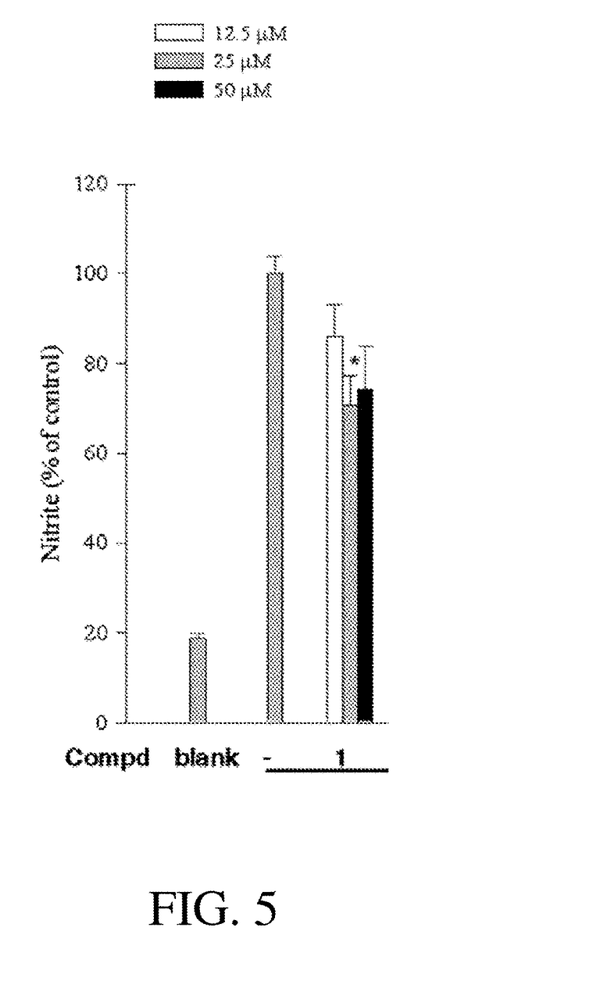
FIG. 5 shows the effect of isolated compounds on NO production from LPS-stimulated RAW264.7 cells. Values are expressed as the means±SD of three independent experiments, each with triplicates and statistically are analyzed using Student's t-test. *$p<0.05$, indicates a significant difference from the control. RAW264.7 cells are stimulated by 1 µg/ml of LPS for 24 h of incubation.

The isolated compound I is tested for LPS-stimulated NO production in RAW264.7 at 12.5, 25 and 50 µM, respectively (FIG. 5). The result suggests that the flavonoid in adlay bran partially, at least, contributed to its anti-inflammatory effect. This is the first report of polymethoxyflavones being isolated from a cereal, and their various bioactivities mean that adlay can be used as a functional food.

LC/MS Identified Major Flavonoids in the ABE-EtOAc

Figure 6:
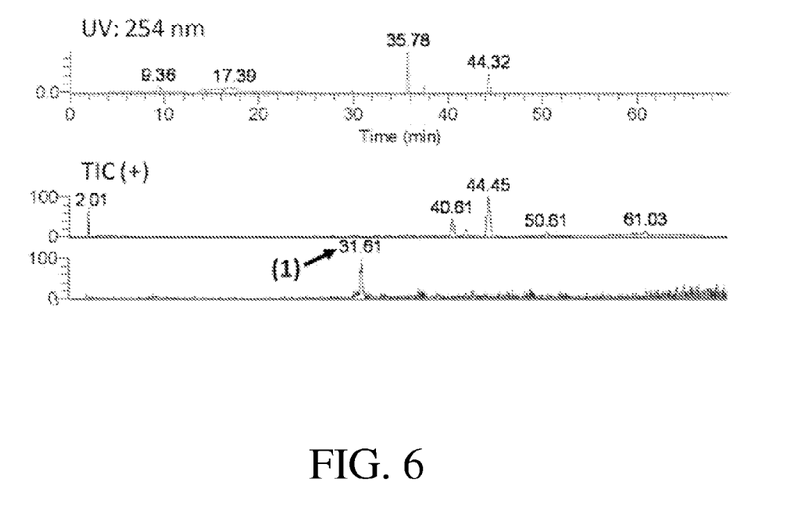
FIG. 6 shows the HPLC and LC/MS chromatography total positive ion currents of flavonoid-enriched fractions by HPLC/MS. (1) 2',6-dihydroxy-4'-methoxydihydroauronol.

2',6-dihydroxy-4'-methoxydihydroauronol is analyzed by LC/MS. In FIG. 6, the UV chromatogram and total ion current (TIC) of the LC/MS for the bioactive fraction are shown. As shown in FIG. 6, 2',6-dihydroxy-4'-methoxydihydroauronol ($t_R$=31.61 min, [M+H]$^+$ m/z, 289) is analyzed in the positive ion mode.

CONCLUSIONS

LPS-stimulated production of inflammatory mediators, in both RAW 264.7 cells and murine peritoneal macrophages, is used as a screening platform. iNOS and cytokine productions of IL-6 and TNF-α are targeted molecules, to examine the anti-inflammatory effects of adlay bran extract and the bioactive subfractions. The present results show that the higher-polarity subfractions of the ABE-EtOAc potently inhibited NO synthesis (FIG. 3A). LPS stimulates both IL-6 and TNF-α secretions in is RAW264.7 cells and peritoneal macrophages (FIG. 4) with no direct cytotoxicity at the treated concentrations. Using column chromatography, 2',6-dihydroxy-4'-methoxydihydroauronol is isolated and identified from the active fraction. 2',6-dihydroxy-4'-methoxydihydroauronol is further tested for inhibition of NO production in RAW264.7 cells (FIG. 5). These results showed that 2',6-dihydroxy-4'-methoxydihydroauronol is the major components of the ABE-EtOAc responsible for the anti-inflammatory activities.

This is the first investigation of the anti-inflammation activity and chemical components of adlay bran. Our results suggest that flavonoids in adlay bran contributed, at least partially, to its anti-inflammatory effect. Thus, adlay bran is a source of natural inflammatory inhibitors, and is beneficial to the health of consumers.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the following claims.

What is claimed is:

1. A flavonoid of formula (I):

formula (I)

wherein $R_1$ is H or an alkyl group having 1 to 6 carbon atoms.

2. The flavonoid according to claim 1, wherein $R_1$ is a methyl group.

3. A composition comprising the flavonoid according to claim 1 and optionally a pharmaceutically acceptable carrier or excipient.

4. The composition according to claim 3, wherein $R_1$ is a methyl group.

5. The composition according to claim 3, wherein the flavonoid is provided in the form of an alcohol extract of dehulled adlay seeds.

6. The composition according to claim 5, wherein the flavonoid is provided in the form of an ethyl acetate sub-fraction of the alcohol extract of dehulled adlay seeds.

7. The composition according to claim 5, wherein the adlay is *Coix lachryma-jobi* L. var. *ma-yuen* Stapf.

8. The composition according to claim 5, wherein the alcohol is selected from the group consisting of methanol, ethanol, n-propanol, isopropanol, n-butanol, iso-butanol, sec-butanol, tert-butanol, and ethanol acetate.

9. A process for the preparation of the flavonoid according to claim 1, which process comprises the steps of:
    (a) providing adlay bran from dehulled adlay seeds;
    (b) extracting the adlay bran in step (a) with an alcohol solution to obtain an alcohol extract;
    (c) sequential partitioning the ethanol extract in step (b) with hexane and ethyl acetate to obtain an ethyl acetate fraction;
    (d) subfractioning the ethyl acetate fraction in step (c) with column chromatography with successive elution by an ethyl acetate/hexane gradient ant methanol solvent to obtain an about 40% to about 60% ethyl acetate/hexane subfration; and
    (e) isolating the flavonoid from the subfraction in step (d) by high-performance liquid chromatography.

10. The process according to claim 9, wherein the adlay is *Coix lachryma-jobi* L. var. *ma-yuen* Stapf.

11. The process according to claim 9, wherein the alcohol is selected from the group consisting of methanol, ethanol, n-propanol, isopropanol, n-butanol, iso-butanol, sec-butanol, tert-butanol, and ethanol acetate.

12. A method for treating inflammation in a subject, which comprises administering to said subject an effective amount of the flavonoid according to claim 1 and a pharmaceutically acceptable carrier or excipient.

13. The method according to claim 12, wherein $R_1$ is a methyl group.

* * * * *